United States Patent

Tegels

(10) Patent No.: US 9,492,156 B2
(45) Date of Patent: Nov. 15, 2016

(54) LARGE BORE ANCHOR DEVICE

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 211 days.

(21) Appl. No.: 13/682,575

(22) Filed: Nov. 20, 2012

(65) Prior Publication Data

US 2013/0138149 A1    May 30, 2013

Related U.S. Application Data

(60) Provisional application No. 61/564,237, filed on Nov. 28, 2011.

(51) Int. Cl.
*A61B 17/04* (2006.01)
*A61B 17/00* (2006.01)

(52) U.S. Cl.
CPC ........ *A61B 17/0401* (2013.01); *A61B 17/0057* (2013.01); *A61B 2017/00654* (2013.01);
(Continued)

(58) Field of Classification Search
CPC .......... A61B 17/0401; A61B 17/0057; A61B 17/1214; A61B 17/12159; A61B 2017/00659; A61B 2017/00778; A61B 2017/00862; A61B 2017/00867; A61B 2017/00871; A61B 2017/00884; A61B 2017/0406; A61B 2017/00637; A61B 2017/00654; A61B 2017/00592; A61B 2017/00641

USPC ....... 606/142, 144, 139, 151, 184, 213, 214, 606/215, 232; 604/35, 39
See application file for complete search history.

(56) References Cited

U.S. PATENT DOCUMENTS 3,470,875 A    10/1969    Johnson
4,556,060 A *  12/1985    Perlin ................ A61B 17/1227
                                                24/552

(Continued)

FOREIGN PATENT DOCUMENTS

EP    0818178 A2    1/1998
EP    1158907 A1    12/2001

(Continued)

OTHER PUBLICATIONS

PCT Communication Relating to the Results of the Partial International Search for International Application No. PCT/US2012/041196, mailed Sep. 11, 2012.

(Continued)

*Primary Examiner* — Katherine M Shi
*Assistant Examiner* — Mohamed Gabr
(74) *Attorney, Agent, or Firm* — Holland & Hart

(57) ABSTRACT

A vascular closure system includes a suture and an anchor assembly. The anchor assembly includes a first anchor portion having a plurality of petal members automatically expandable from a retracted position for delivery through a vessel puncture in a vessel, and an expanded position when deployed within the vessel. The anchor assembly also includes a second anchor portion connected to the suture and positioned distal of the first anchor portion within the vessel. Withdrawing the suture pulls the second anchor portion against the first anchor portion to contact the first anchor portion against an inner surface of the vessel adjacent to the vessel puncture. The vascular closure system may also include an automatic compaction assembly that automatically compacts a sealing member against the anchor assembly to seal closed the vessel puncture upon withdrawal of the vascular closure system.

13 Claims, 12 Drawing Sheets

(52) U.S. Cl.
CPC ........... *A61B2017/00659* (2013.01); *A61B 2017/00778* (2013.01); *A61B 2017/00862* (2013.01); *A61B 2017/00867* (2013.01); *A61B 2017/00871* (2013.01); *A61B 2017/00884* (2013.01); *A61B 2017/0406* (2013.01)

(56) References Cited

U.S. PATENT DOCUMENTS

| | | | |
|---|---|---|---|
| 5,021,059 A * | 6/1991 | Kensey | A61B 17/0057 604/15 |
| 5,192,301 A * | 3/1993 | Kamiya | A61B 17/0057 604/907 |
| 5,304,184 A * | 4/1994 | Hathaway | A61B 17/0057 606/144 |
| 5,312,435 A * | 5/1994 | Nash | A61B 17/0057 604/15 |
| 5,431,666 A | 7/1995 | Sauer et al. | |
| 5,520,702 A | 5/1996 | Sauer et al. | |
| 5,531,759 A * | 7/1996 | Kensey | A61B 17/0401 604/15 |
| 5,545,178 A * | 8/1996 | Kensey | A61B 17/0401 604/15 |
| 5,562,686 A | 10/1996 | Sauer et al. | |
| 5,593,422 A * | 1/1997 | Muijs Van de Moer | A61B 17/0057 604/285 |
| 5,613,974 A | 3/1997 | Andreas et al. | |
| 5,643,292 A | 7/1997 | Hart | |
| 5,649,959 A * | 7/1997 | Hannam | A61B 17/0057 604/181 |
| 5,662,681 A * | 9/1997 | Nash | A61B 17/0057 604/285 |
| 5,674,231 A | 10/1997 | Green et al. | |
| 5,690,674 A * | 11/1997 | Diaz | A61B 17/0057 604/285 |
| 5,700,273 A | 12/1997 | Buelna et al. | |
| 5,709,692 A | 1/1998 | Mollenauer et al. | |
| 5,728,114 A * | 3/1998 | Evans | A61B 17/0057 128/887 |
| 5,766,183 A | 6/1998 | Sauer | |
| 5,860,990 A | 1/1999 | Nobles et al. | |
| 5,893,369 A * | 4/1999 | LeMole | A61B 17/11 606/184 |
| 5,922,009 A * | 7/1999 | Epstein | A61B 17/00491 606/213 |
| 5,972,005 A | 10/1999 | Stalker et al. | |
| 6,036,699 A | 3/2000 | Andreas et al. | |
| 6,036,720 A * | 3/2000 | Abrams | A61B 17/12022 606/200 |
| 6,045,569 A | 4/2000 | Kensey et al. | |
| 6,045,570 A * | 4/2000 | Epstein | A61B 17/00491 606/214 |
| 6,059,800 A * | 5/2000 | Hart | A61B 17/0469 606/139 |
| 6,090,130 A | 7/2000 | Nash et al. | |
| 6,136,010 A | 10/2000 | Modesitt et al. | |
| 6,165,196 A * | 12/2000 | Stack | A61B 17/11 606/194 |
| 6,171,319 B1 * | 1/2001 | Nobles | A61B 17/11 606/151 |
| 6,334,865 B1 * | 1/2002 | Redmond | A61B 17/0057 606/139 |
| 6,355,050 B1 | 3/2002 | Andreas et al. | |
| 6,383,174 B1 * | 5/2002 | Eder | A61B 17/12022 606/1 |
| 6,562,052 B2 | 5/2003 | Nobles et al. | |
| 6,582,453 B1 * | 6/2003 | Tran | A61B 17/0401 606/232 |
| 6,623,509 B2 | 9/2003 | Ginn | |
| 6,641,592 B1 | 11/2003 | Sauer et al. | |
| 6,896,692 B2 * | 5/2005 | Ginn | A61B 17/0057 606/213 |
| 6,911,034 B2 | 6/2005 | Nobles et al. | |
| 6,932,824 B1 * | 8/2005 | Roop | A61B 17/0057 606/139 |
| 6,964,668 B2 | 11/2005 | Modesitt et al. | |
| 6,969,397 B2 * | 11/2005 | Ginn | A61B 17/0057 600/585 |
| 7,001,400 B1 | 2/2006 | Modesitt et al. | |
| 7,083,635 B2 | 8/2006 | Ginn | |
| 7,235,087 B2 | 6/2007 | Modesitt et al. | |
| 7,250,057 B2 * | 7/2007 | Forsberg | A61B 17/0057 475/125 |
| 7,341,595 B2 * | 3/2008 | Hinchliffe | A61B 17/0057 606/151 |
| 7,361,183 B2 | 4/2008 | Ginn | |
| 7,390,328 B2 | 6/2008 | Modesitt | |
| 7,410,482 B2 * | 8/2008 | Murphy | A61B 17/12022 606/1 |
| 7,553,319 B2 | 6/2009 | Bagaoisan et al. | |
| 7,601,161 B1 | 10/2009 | Nobles et al. | |
| 7,618,436 B2 * | 11/2009 | Forsberg | A61B 17/0057 606/213 |
| 7,618,438 B2 * | 11/2009 | White | A61B 17/0057 606/232 |
| 7,621,937 B2 | 11/2009 | Pipenhagen et al. | |
| 7,686,821 B2 | 3/2010 | Hathaway et al. | |
| 7,731,726 B2 * | 6/2010 | Belhe | A61B 17/0057 606/144 |
| 7,744,610 B2 | 6/2010 | Hausen | |
| 7,752,853 B2 | 7/2010 | Singh et al. | |
| 7,753,933 B2 * | 7/2010 | Ginn | A61B 17/0057 606/213 |
| 7,837,696 B2 | 11/2010 | Modesitt et al. | |
| 7,842,047 B2 | 11/2010 | Modesitt et al. | |
| 7,842,048 B2 | 11/2010 | Ma | |
| 7,846,170 B2 | 12/2010 | Modesitt et al. | |
| 7,850,701 B2 | 12/2010 | Modesitt et al. | |
| 7,850,710 B2 * | 12/2010 | Huss | A61B 17/0057 606/213 |
| 7,883,517 B2 | 2/2011 | Pantages et al. | |
| 7,931,670 B2 | 4/2011 | Fiehler et al. | |
| 7,985,240 B2 | 7/2011 | Bagaoisan et al. | |
| 8,029,476 B2 | 10/2011 | Rosenberg et al. | |
| 8,048,092 B2 | 11/2011 | Modesitt et al. | |
| 8,048,108 B2 * | 11/2011 | Sibbitt, Jr. | A61B 17/0057 606/213 |
| 8,070,772 B2 * | 12/2011 | McGuckin, Jr. | A61B 17/0057 606/151 |
| 8,083,768 B2 | 12/2011 | Ginn et al. | |
| 8,114,125 B2 * | 2/2012 | Seibold | A61B 17/0057 606/215 |
| 8,128,652 B2 * | 3/2012 | Paprocki | A61B 17/0057 606/213 |
| 8,192,456 B2 | 6/2012 | Holman et al. | |
| 8,257,390 B2 * | 9/2012 | Carley | A61B 17/0057 606/213 |
| 8,348,971 B2 * | 1/2013 | Khanna | A61B 17/0057 606/213 |
| 8,382,795 B2 * | 2/2013 | Forsberg | A61B 17/0057 606/213 |
| 8,425,553 B2 * | 4/2013 | Michlitsch | A61B 17/00491 606/213 |
| 8,439,944 B2 * | 5/2013 | Yassinzadeh | A61B 17/0057 606/198 |
| 8,443,808 B2 * | 5/2013 | Brenzel | A61B 17/12022 128/830 |
| 8,444,673 B2 * | 5/2013 | Thielen | A61B 17/0057 606/213 |
| 8,506,592 B2 * | 8/2013 | Killion | A61B 17/00491 606/213 |
| 8,545,530 B2 * | 10/2013 | Eskridge | A61B 17/12022 606/191 |
| 8,647,365 B2 * | 2/2014 | Tegels | A61B 17/0057 606/213 |
| 8,652,166 B2 * | 2/2014 | Åkerfeldt | A61B 17/0057 606/139 |
| 8,685,059 B2 * | 4/2014 | Walters | A61B 17/0057 606/213 |
| 8,758,398 B2 * | 6/2014 | Carley | A61B 17/0644 606/142 |
| 8,758,400 B2 * | 6/2014 | Ginn | A61B 17/0057 606/213 |

(56) References Cited

U.S. PATENT DOCUMENTS

| | | | |
|---|---|---|---|
| 8,758,402 B2* | 6/2014 | Jenson | A61B 17/0057 606/213 |
| 9,107,646 B2* | 8/2015 | Tegels | A61B 17/0057 |
| 2001/0003158 A1* | 6/2001 | Kensey | A61B 17/0057 606/213 |
| 2004/0044364 A1* | 3/2004 | DeVries | A61B 17/064 606/213 |
| 2005/0085854 A1 | 4/2005 | Ginn | |
| 2005/0125031 A1* | 6/2005 | Pipenhagen | A61B 17/0057 606/213 |
| 2005/0267528 A1* | 12/2005 | Ginn | A61B 17/0057 606/214 |
| 2005/0288786 A1* | 12/2005 | Chanduszko | A61B 17/0057 623/11.11 |
| 2006/0135991 A1* | 6/2006 | Kawaura | A61B 17/0057 606/213 |
| 2006/0212071 A1 | 9/2006 | Ginn et al. | |
| 2006/0241579 A1* | 10/2006 | Kawaura | A61B 17/0057 606/39 |
| 2006/0265007 A1* | 11/2006 | White | A61B 17/0057 606/232 |
| 2007/0073343 A1* | 3/2007 | Jahns et al. | 606/232 |
| 2007/0073344 A1* | 3/2007 | Jahns | A61B 17/0482 606/232 |
| 2008/0065151 A1* | 3/2008 | Ginn | A61B 17/0057 606/213 |
| 2009/0012541 A1* | 1/2009 | Dahl | A61B 17/0401 606/151 |
| 2009/0039138 A1* | 2/2009 | Bender | A61B 17/0057 227/179.1 |
| 2009/0099578 A1 | 4/2009 | Heneveld et al. | |
| 2009/0149716 A1* | 6/2009 | Diao | A61B 1/00085 600/202 |
| 2009/0171282 A1* | 7/2009 | Pipenhagen | A61B 17/0057 604/103.01 |
| 2009/0216271 A1* | 8/2009 | Zipper | A61B 17/0487 606/232 |
| 2009/0287229 A1* | 11/2009 | Ogdahl | A61B 17/0401 606/151 |
| 2009/0306685 A1 | 12/2009 | Fill | |
| 2009/0318904 A9* | 12/2009 | Cooper | A61B 8/445 606/1 |
| 2010/0042118 A1 | 2/2010 | Garrison et al. | |
| 2010/0179571 A1* | 7/2010 | Voss | A61B 17/0057 606/142 |
| 2010/0228184 A1* | 9/2010 | Mavani | A61B 17/0057 604/35 |
| 2010/0234883 A1* | 9/2010 | White | A61B 17/0057 606/213 |
| 2011/0009900 A1* | 1/2011 | Holman | A61B 17/0057 606/213 |
| 2011/0046663 A1* | 2/2011 | Zhou | A61B 17/0057 606/213 |
| 2011/0071567 A1 | 3/2011 | Modesitt et al. | |
| 2011/0087272 A1* | 4/2011 | Sargeant | A61B 17/0057 606/213 |
| 2011/0144445 A1* | 6/2011 | Brockmeier | A61B 17/3498 600/208 |
| 2011/0224719 A1* | 9/2011 | Fortson | A61B 17/0057 606/213 |
| 2012/0095494 A1* | 4/2012 | Dominguez | A61F 5/0033 606/192 |
| 2012/0197292 A1* | 8/2012 | Chin-Chen | A61B 17/0057 606/213 |
| 2012/0226309 A1* | 9/2012 | Jonsson | A61B 17/0057 606/213 |
| 2013/0123826 A1* | 5/2013 | Kramer | A61B 17/3478 606/185 |
| 2013/0138149 A1* | 5/2013 | Tegels | A61B 17/0401 606/232 |
| 2013/0190803 A1* | 7/2013 | Angel | A61B 5/0066 606/200 |
| 2014/0046220 A1* | 2/2014 | Nelson | A61B 17/0057 600/587 |
| 2014/0142619 A1* | 5/2014 | Serina | A61B 1/00078 606/213 |
| 2015/0005809 A1* | 1/2015 | Ayres | A61F 2/01 606/200 |
| 2015/0039084 A1* | 2/2015 | Levi | A61B 17/0057 623/2.38 |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 | 2/1997 |
| WO | 0051498 | 9/2000 |
| WO | 0078226 A1 | 12/2000 |
| WO | 2010081106 A1 | 7/2010 |

OTHER PUBLICATIONS

Notification of Transmittal of the International Search Report and the Written Opinion of the International Searching Authority, or the Declaration for International Application No. PCT/US2012/064768, mailed Feb. 19, 2013, (18 pp.).

Notification of Transmittal of the International Search Report and the Written Opinion of the International Searching Authority, or the Declaration for International Application No. PCT/US2012/066012, mailed Feb. 19, 2013, (17 pp.).

Notification of Transmittal of the International Search Report and the Written Opinion of the International Searching Authority, or the Declaration for International Application No. PCT/US2012/064770, mailed Feb. 19, 2013, (16 pp.).

* cited by examiner

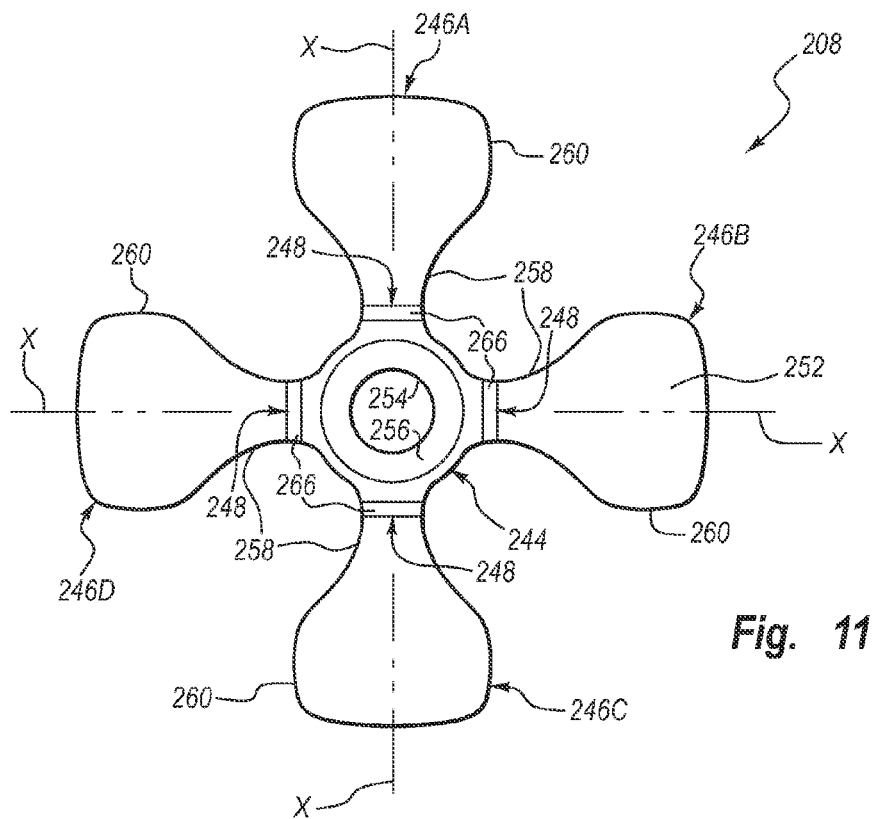
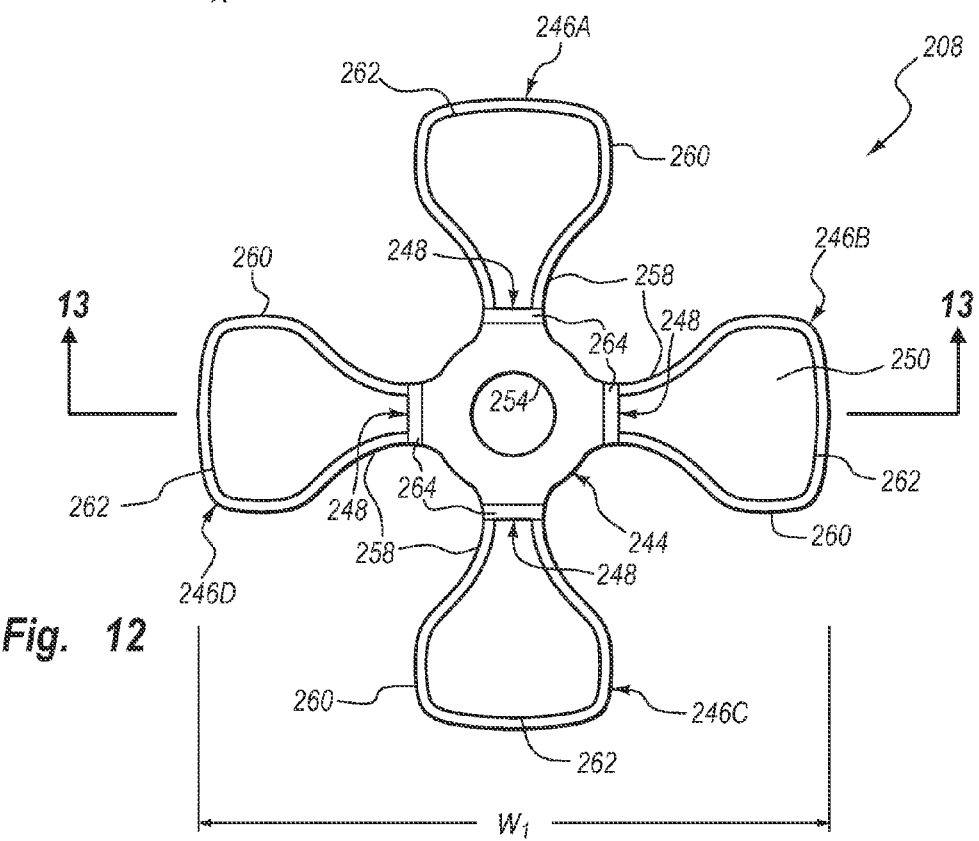
Fig. 11
Fig. 12

LARGE BORE ANCHOR DEVICE

CROSS REFERENCE RELATED APPLICATIONS

This application claims the benefit of U.S. Provisional App. No. 61/564,237, filed 28 Nov. 2011, which is incorporated herein in its entirety by this reference.

TECHNICAL FIELD

The present disclosure relates to closure devices, and more specifically relates to closure devices that seal closed a tissue puncture such as a vascular puncture.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place sealing material at the tissue puncture site. Successful deployment of the sealing material includes ejection from within the closure device sheath to a location adjacent to the tissue puncture along an outer surface of the vessel. Failure to contact the sealing material against the outer surface of the vessel may also result in an improper seal.

Intravascular devices typically include an intravascular component (e.g., anchor) used to create a compressive sealing force between the inner wall of the artery and the exterior device. The opposite applied force from the intravascular component helps place the sealing material in alignment with the tissue puncture and obtain a proper seal. The intravascular component may be permanently positioned within the vessel to help maintain tension that holds the sealing material in place to maintain the seal. There are challenges involved in providing an intravascular component that is small enough for delivery through the tissue puncture while still being large enough to provide proper anchoring within the vessel. Other challenges exist related to maintaining a position of the intravascular component in contact with an inner surface of the vessel, and connecting the intravascular component to the sealing material.

SUMMARY

One aspect of the present disclosure relates to a vascular closure system that includes a suture and an anchor assembly. The anchor assembly includes a first anchor portion having a plurality of petal members automatically expandable from a retracted position for delivery through a vessel puncture in a vessel, and an expanded position when deployed within the vessel. The anchor assembly also includes a second anchor portion connected to the suture and positioned distal of the first anchor portion within the vessel. Withdrawing the suture pulls the second anchor portion against the first anchor portion to contact the first anchor portion against an inner surface of the vessel adjacent to the vessel puncture.

The plurality of petal members may be oriented perpendicular to a longitudinal dimension of the anchor assembly when in the expanded position. The plurality of petal members may extend proximally when in the retracted position. The plurality of petal members may pivot in a single direction from the expanded position to the retracted position. The plurality of petal members may each include a living hinge. The first anchor portion may include an aperture defined by a first tapered surface, and the second anchor portion may include a second tapered surface that contacts the first tapered surface.

The first and second anchor portions may be separate and distinct pieces. The second anchor portion may include a suture through hole configured for connecting the suture to the second anchor portion. At least some of the plurality of petal members may include a suture aperture configured to pass a suture therethrough. The plurality of petal members may include a stiffening rib.

Another aspect of the present disclosure relates to a vascular closure device that includes a suture, a two-piece anchor assembly, and a sealing member. The anchor assembly includes a first anchor portion having a plurality of petal members that pivot into an expanded position upon positioning in a vessel, and a second anchor portion connected to the suture and configured to draw the first anchor portion against an inner surface of the vessel upon withdrawal of the second anchor portion. The sealing member is configured to advance along the suture and be compacted against the anchor assembly to seal closed a vessel puncture.

The plurality of petal members may each include a hinge portion. The plurality of petal members may each include a neck portion and a petal portion, wherein the neck portion has a smaller maximum width than a maximum width of the petal portion. The first anchor portion may comprise a shape memory material. The first anchor portion may have a larger profile when in the expanded position than a profile of the second anchor portion.

A further aspect of the present disclosure relates to a method of closing an opening in a wall of a vessel. The method includes providing an anchor assembly, a suture, and a sealing member, wherein the anchor assembly includes a first anchor member having a plurality of petals movable between expanded and retracted positions, and a second anchor member connected to the suture. The method also includes advancing the anchor assembly through the vessel opening and into the vessel, moving the plurality of petals into the expanded position, retracting the second anchor member to draw the first anchor member against an inner surface of the vessel wall, and advancing the sealing member to the vessel opening to seal closed the vessel puncture.

Moving the plurality of petals into the expanded position may occur automatically upon deploying the first anchor member within the vessel. The method may include providing a carrier tube and positioning the anchor assembly within the carrier tube for delivery into the vessel. The method may include pivoting the plurality of petals proximally into a retracted position before advancing the anchor assembly through the vessel opening. The method may include pivoting the plurality of petals through an angle of no greater than 100° between the expanded and retracted positions.

The foregoing and other features, utilities, and advantages of the invention will be apparent from the following detailed description of the invention with reference to the accompanying drawings.

BRIEF DESCRIPTION OF THE DRAWINGS

FIG. 11 is a front view of a first anchor portion of the anchor assembly of FIGS. 6-10.

FIG. 12 is a rear view of a first anchor portion of the anchor assembly of FIGS. 6-10.

DETAILED DESCRIPTION

Figure 1:
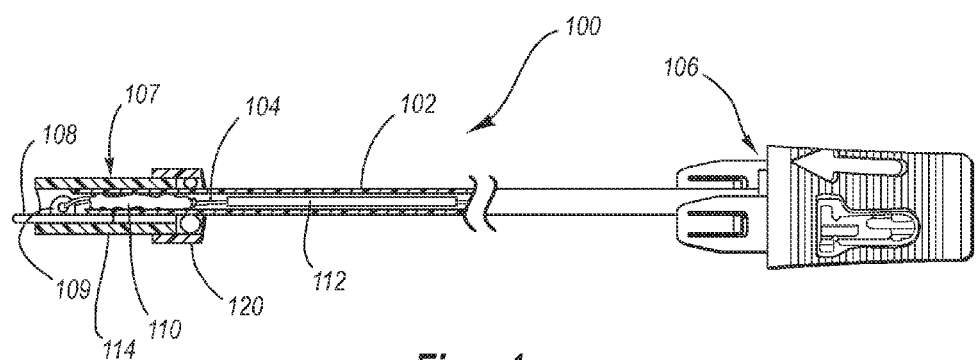
FIG. 1 is a partial cut-away side view of a tissue puncture closure device according to the prior art.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not intended to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "compact," "compaction," and "compacting" are used broadly to mean packing down and compressing by one or a succession of blows or taps or smooth, steady pressure, but not by excessive force. The terms "tamp" and "tamping" may relate to certain types or forms of "compaction" and "compacting." "Engage" and "engabable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc. While the vascular instruments shown and described below include puncture closure devices, the application of principles described herein are not limited to the specific devices shown. The principles described herein may be used with any medical device. Therefore, while the description below is directed primarily to arterial procedures and certain embodiments of a tissue puncture closure device, the methods and apparatus are only limited by the appended claims.

The present disclosure is directed to a closure device that places an anchor assembly through a tissue puncture in a tissue layer to assist in sealing closed the tissue puncture. In one embodiment, the anchor assembly includes at least two components, wherein a first of the components includes a plurality of extendable petal members and a second of the components is configured as a plug structure that draws the first component against an inner surface of the tissue layer. The tissue puncture may be a large bore opening sized at least 10 French. The present disclosure contemplates that a medical procedure will be performed through a sheath that is inserted through the tissue puncture in the tissue layer (e.g., vessel wall). The sheath provides access to the inside of the tissue layer. After completion of the medical procedure and removal of the sheath, the closure device positions the anchor assembly through the tissue puncture to provide an anchoring function on one side of the tissue puncture, and positions a sealing member on an opposite side of the tissue puncture to seal closed the tissue puncture.

The petal members of the anchor assembly are movable from a retracted position that provides a reduced profile during delivery of the anchor assembly through the tissue puncture, to an expanded position that provides an enlarged profile to assist in providing an anchoring function. The petal members may automatically move from the retracted position to the expanded position upon being released or deployed once through the tissue puncture. The petal members may retract in a proximal direction. The petal members, when in the expanded position, may extend generally perpendicular to a longitudinal axis of the anchor assembly. The petal members may pivot about hinge members between the retracted and extended positions. The hinge members may include living hinges and be formed integrally with other portions of the first component of the anchor assembly. The petal members may include stiffening members such as at least one rib that, for example, extends around a periphery of the petal member.

Referring to FIGS. 1-4, a tissue puncture closure device 100 is shown according to the prior art. Some example closure devices are disclosed in U.S. Pat. Nos. 7,931,670; 7,618,438; and 7,618,436, which references are incorporated herein in their entireties by this reference. The tissue puncture closure device 100 includes a carrier tube 102 with a filament or suture 104 extending at least partially therethrough. The tissue puncture closure device 100 also includes a first or proximal end 106 and a second or distal end 107. External to the distal end 107 of the carrier tube 102 is an anchor 108. The anchor may include an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may comprise, for example, randomly oriented fibrous material bound together by chemical means. The collagen pad 110 is slidingly attached to the suture 104 as the suture passes distally through the carrier tube 102. As the suture traverses the anchor 108 and reenters the carrier tube 102, the suture 104 is securely slip knotted proximal to the collagen pad 110 to facilitate cinching of the collagen pad 110 when the tissue puncture closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 using a bypass tube 114 that is disposed over the distal end 107 of the carrier tube 102.

Figure 2:
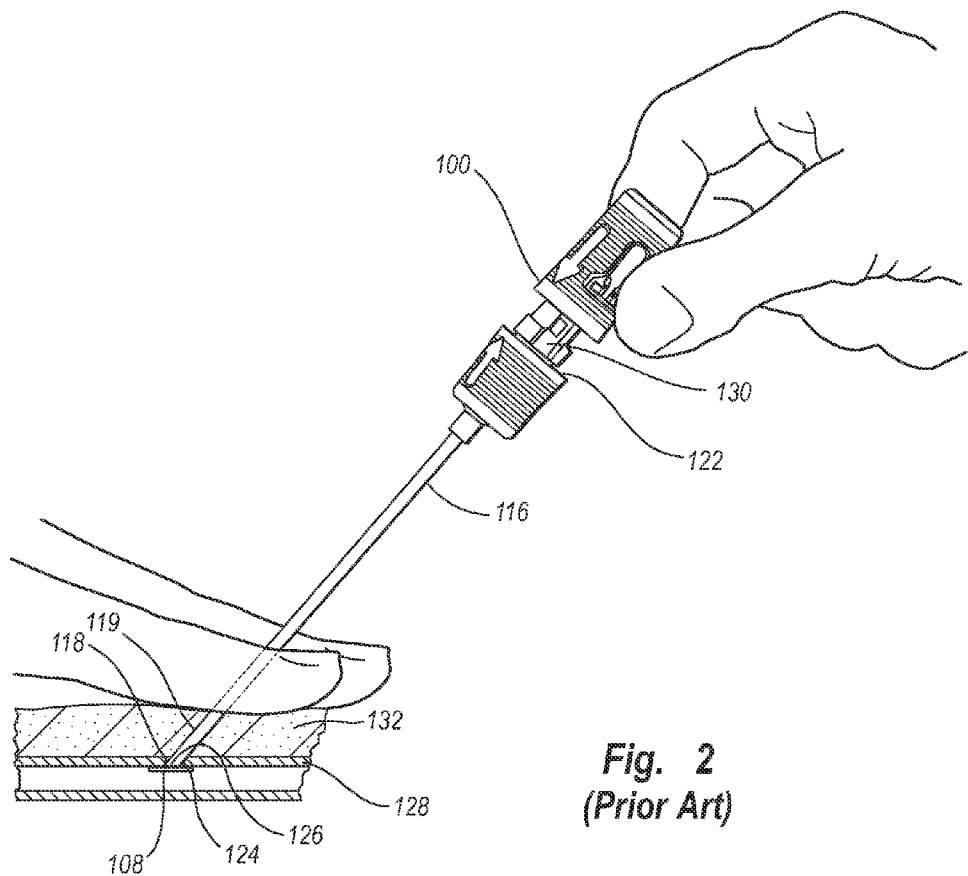
FIG. 2 is a side view of the tissue puncture closure device of FIG. 1 engaged with an artery according to the prior art.
Figure 3:
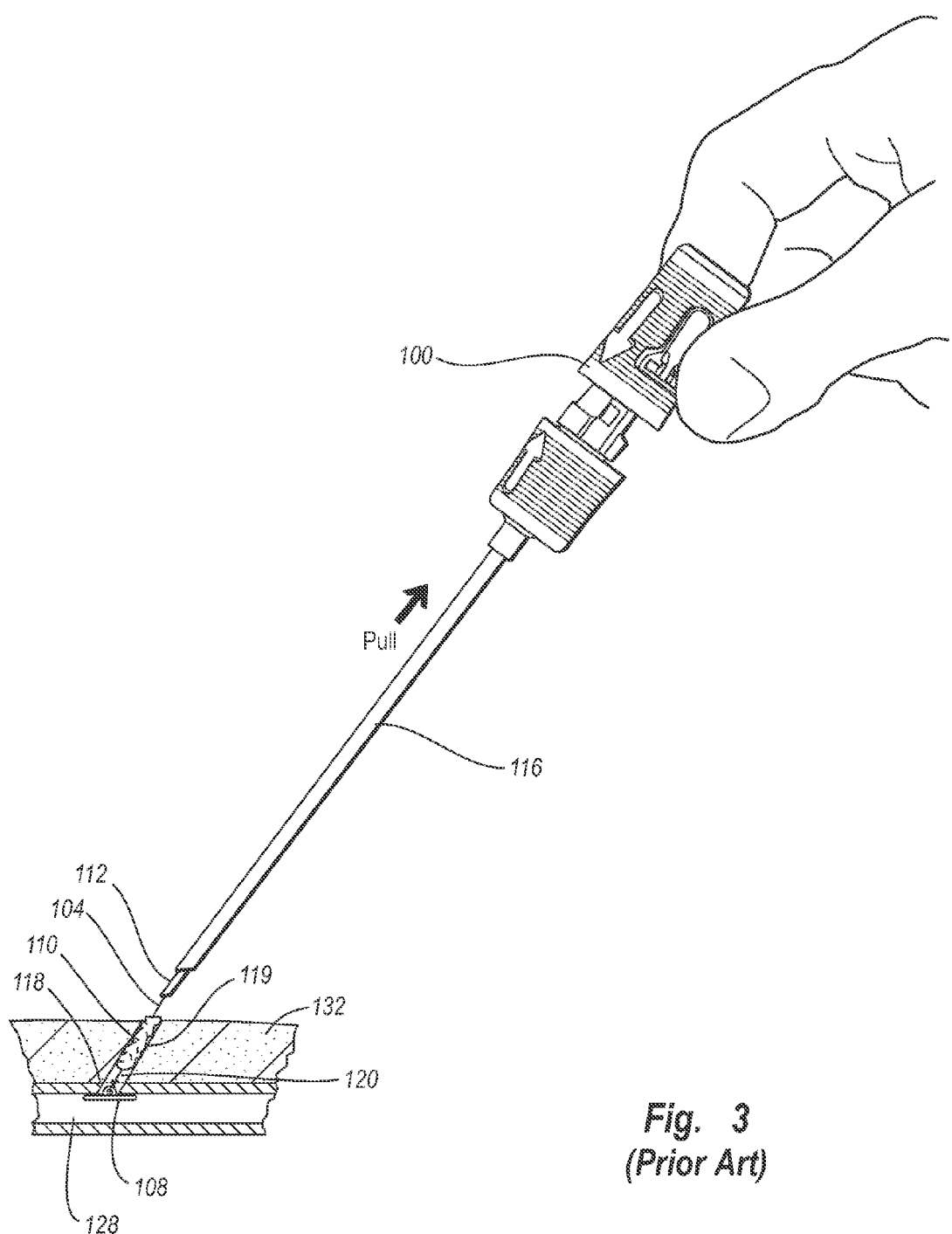
FIG. 3 is a side view of the tissue puncture closure device of FIG. 1 being withdrawn from a vessel according to the prior art to deploy a sealing plug.
Figure 4:
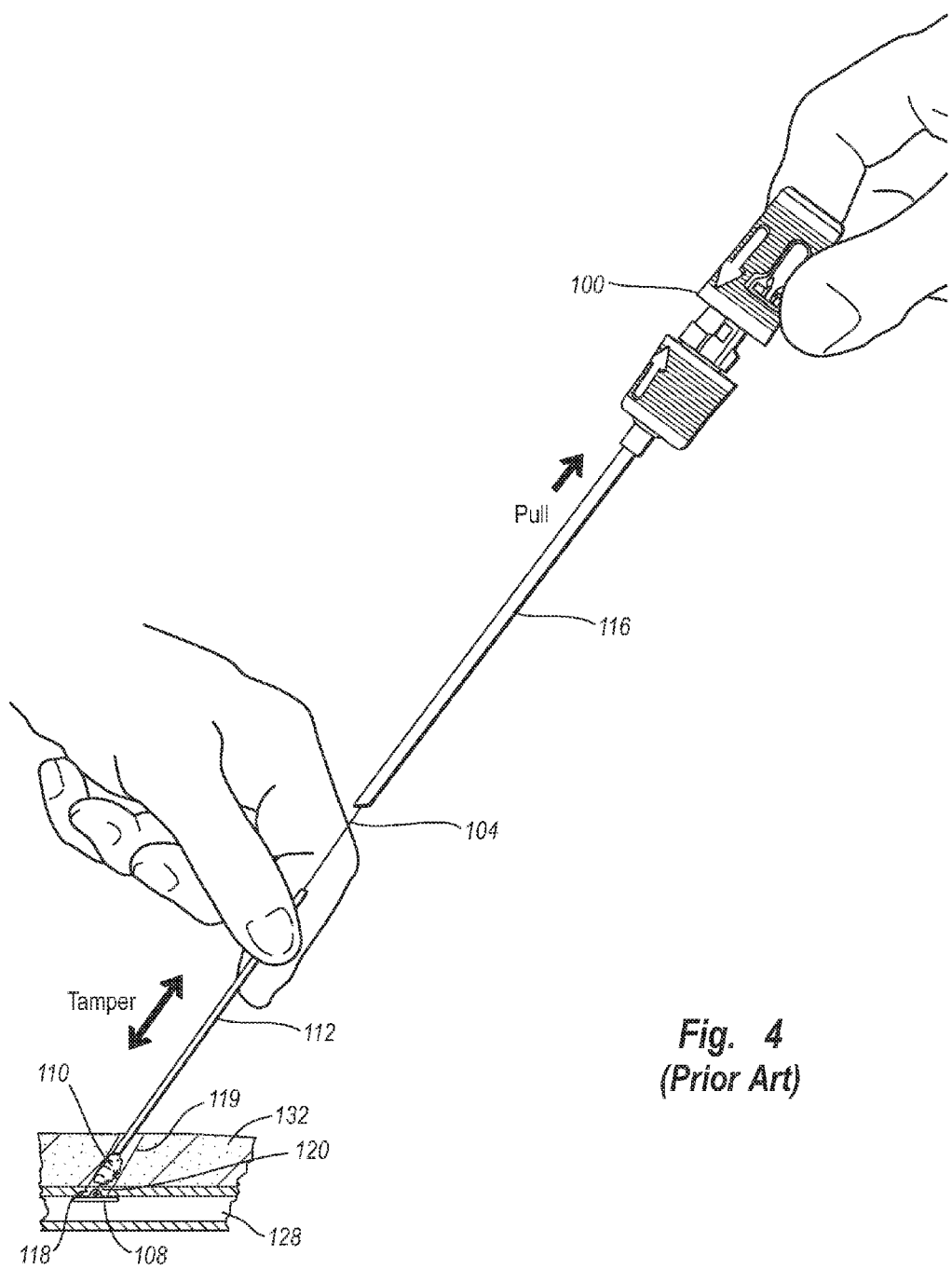
FIG. 4 is a side view of the tissue puncture closure device of FIG. 1 illustrating compaction of the sealing plug according to the prior art.

The flush arrangement of the anchor 108 and carrier tube 102 allows the anchor 108 to be inserted into a sheath such as insertion sheath 116 as shown in FIGS. 2-4, and eventually through a tissue (e.g., arterial) puncture 118. The insertion sheath 116 is shown in FIGS. 2-4 inserted through a percutaneous incision 119 and into an artery 128. The bypass tube 114 (see FIG. 1) includes an oversized head 120 that prevents the bypass tube 114 from passing through an internal passage of the insertion sheath 116. As the tissue puncture closure device 100 is inserted into the insertion sheath 116, the oversized head 120 bears against a surface 122 of insertion sheath 116.

Further insertion of the tissue puncture closure device 100 results in sliding movement between the carrier tube 102 and the bypass tube 114, thereby releasing the anchor 108 from the bypass tube 114 (see FIG. 1). The anchor 108 typically remains in the flush arrangement shown in FIG. 1 following release from the bypass tube 114, limited in movement by the insertion sheath 116.

The insertion sheath 116 may include a monofold 124 at a second or distal end 126 thereof. The monofold acts as a one-way valve to the anchor 108. A monofold is typically a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

The insertion sheath 116 may include a pair of closure device connection apertures (not shown) and a carrier tube aperture (not shown) at a proximal surface 122 (see FIG. 1). The carrier tube 102 is inserted into the carrier tube aperture and the sheath connection members 130 are inserted into and releasably engage with the closure device connection apertures when assembling the tissue puncture closure device 100 with the insertion sheath 116.

Referring next to FIGS. 3-4, with the anchor 108 deployed, the tissue puncture closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 104. The tissue puncture is sandwiched between the anchor 108 and the collagen pad 110, thereby sealing the tissue puncture 118. The suture 104 is then cut and the percutaneous incision 119 may be closed. The suture 104, anchor 108, and collagen pad 110 are generally made of resorbable materials and therefore remain in place while the tissue puncture 118 heals.

It may be difficult to eject and compact the collagen pad 110 using the typical tissue puncture closure device 100 described above. The insertion sheath 116 resists deformation as the collagen pad 110 is ejected from the carrier tube and compaction does not commence until the insertion sheath 116 has been removed so as to expose the compaction member 112 for manual grasping. Under certain conditions, removal of the insertion sheath 116 prior to compacting the collagen pad 110 causes the collagen pad 110 to retract or displace proximally from the tissue puncture 118, creating an undesirable gap between the collagen pad 110 and the tissue puncture 118.

Figure 5:
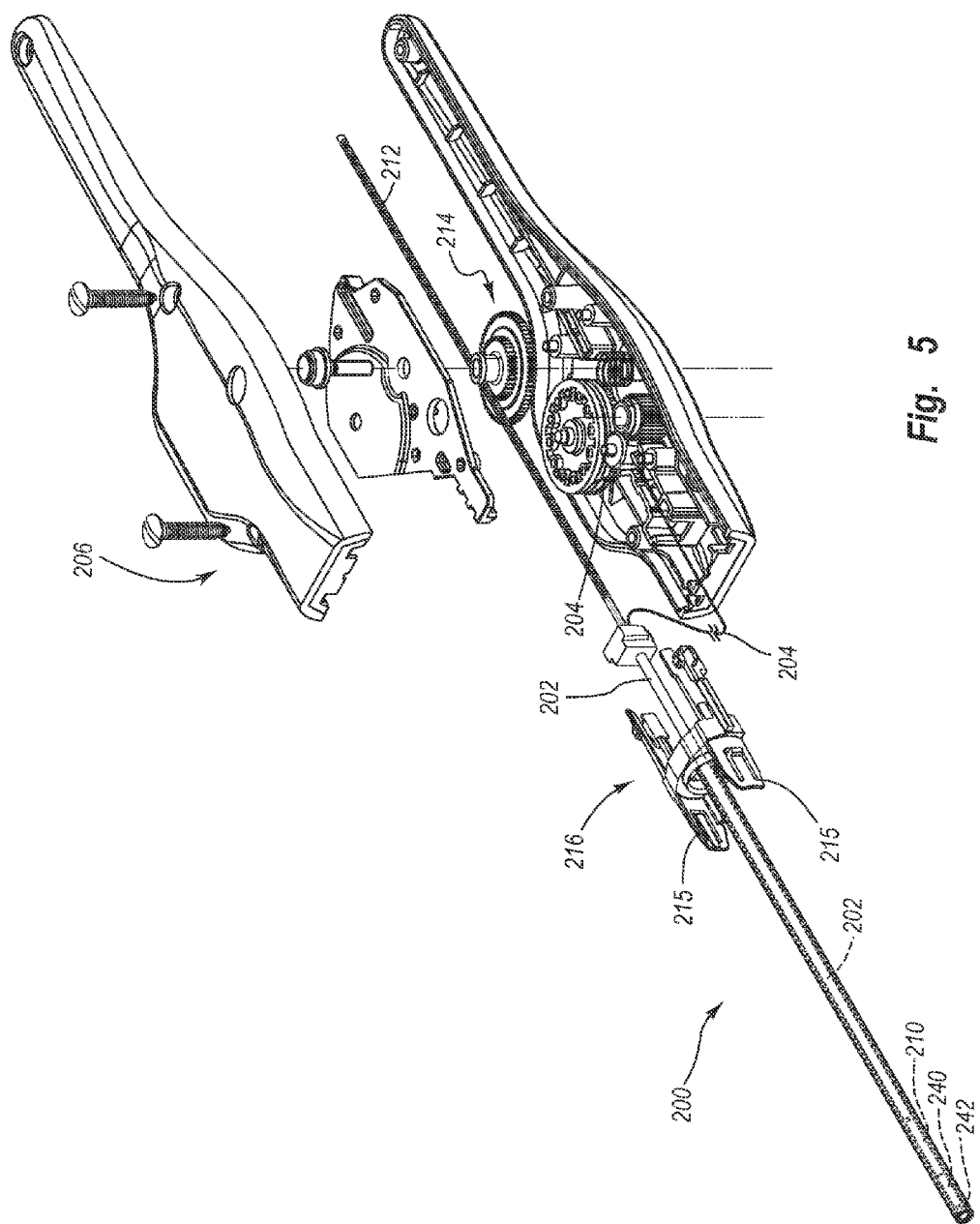
FIG. 5 is an exploded perspective view of an example tissue puncture closure device in accordance with the present disclosure.
Figure 13:
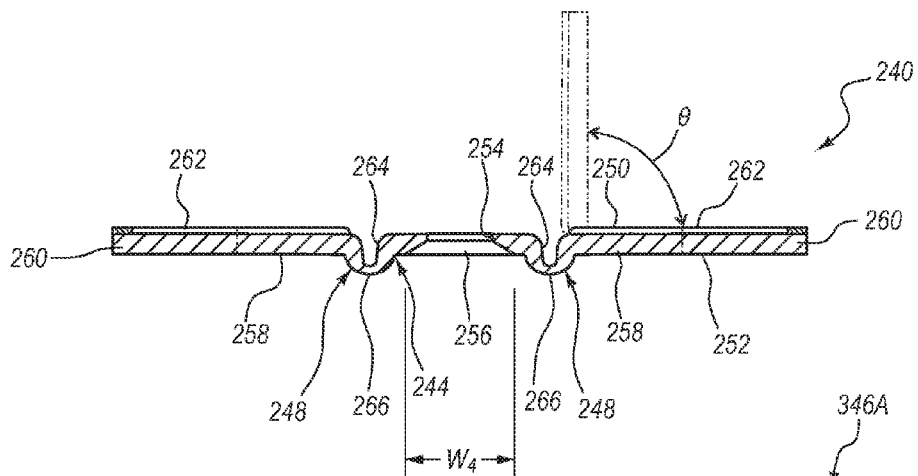
FIG. 13 is a cross-sectional view of the first anchor portion of FIG. 12 taken along cross section indicators 13-13.
Figure 14:
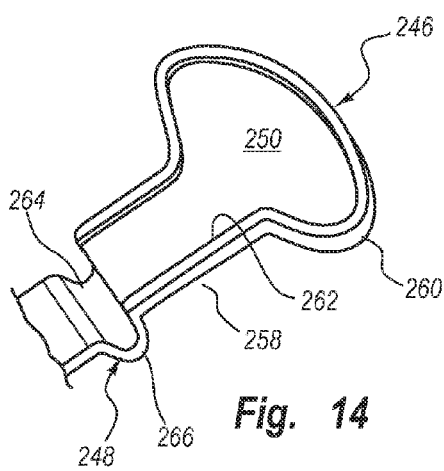
FIG. 14 is a perspective view of a petal member of the first anchor portion of FIGS. 11-13.
Figure 15:
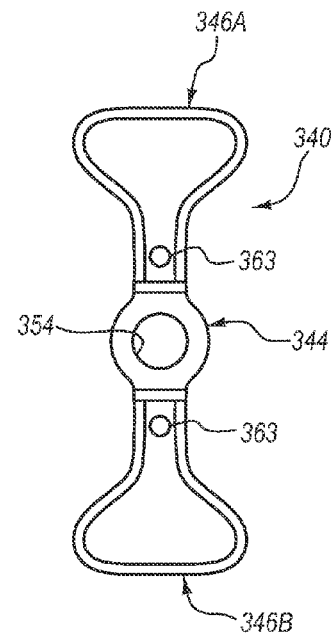
FIG. 15 is a rear view of another example first anchor portion of an anchor assembly in accordance with the present disclosure.
Figure 16:
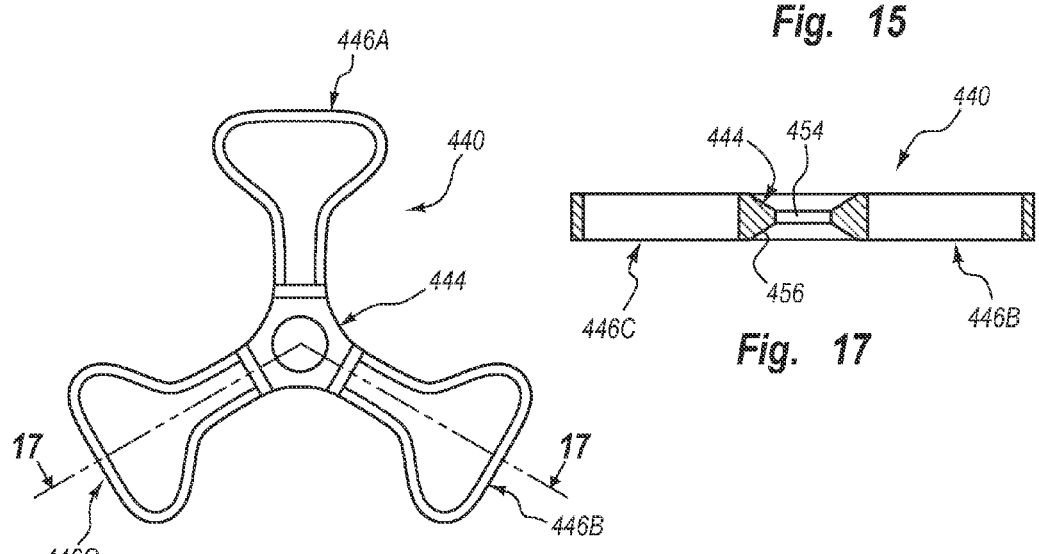
FIG. 16 is a rear view of another example first anchor portion of an anchor assembly in accordance with the present disclosure.
Figure 17:
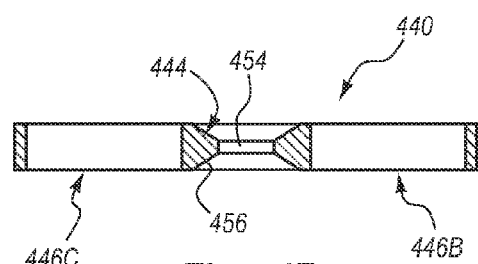
FIG. 17 is a cross-sectional view of the first anchor portion of FIG. 16 taken along cross section indicators 17-17.
Figure 18:
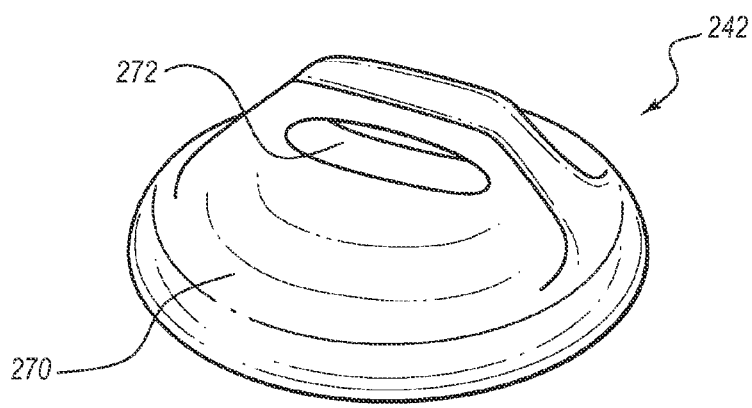
FIG. 18 is a perspective view of a second anchor portion of the anchor assembly of FIGS. 5-10.
Figure 19:
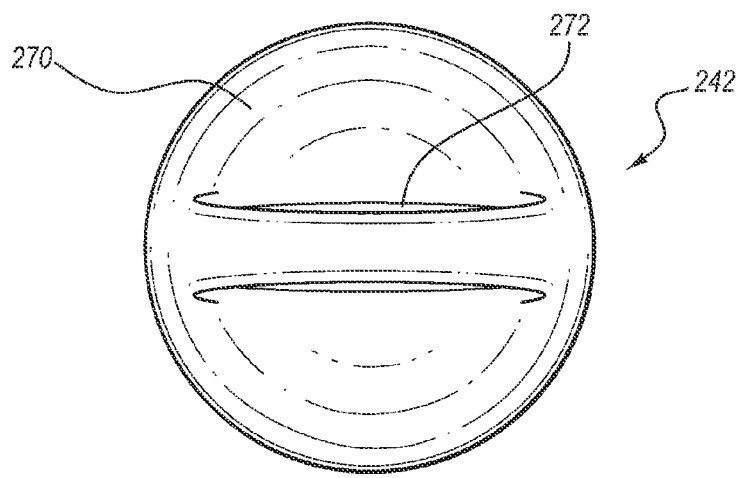
FIG. 19 is a rear view of the second anchor portion of FIG. 18.
Figure 20:
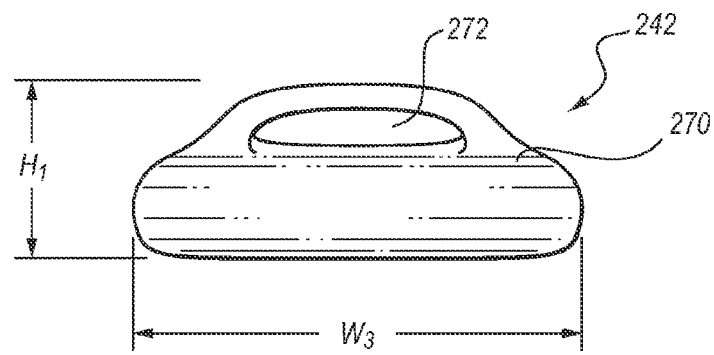
FIG. 20 is a side view of the second anchor portion of FIG. 18.

Referring now to FIGS. 5-14 and 18-20, an apparatus, for example a tissue puncture closure device 200, is shown according to one embodiment of the present disclosure. The closure device 200 is shown as an assembly in the exploded perspective view of FIG. 5. FIGS. 6-10 illustrate the closure device 200 inserted through a procedure sheath 216 and into a vessel 128. FIGS. 11-14 illustrate details of a first portion of an anchor assembly of the closure device 200. FIGS. 15-17 show alternative embodiments of the first portion of the anchor assembly. FIGS. 18-20 illustrate details of a second portion of the anchor assembly of the closure device 200.

The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the closure device 200 according to principles of the present disclosure.

The closure device 200 includes carrier tube 202 designed for insertion through the procedure sheath 216. The carrier tube 202 is used to deliver components of the closure device 200 through the tissue puncture 118 and into the vessel 128. The procedure sheath 216 is designed for insertion through the percutaneous incision 119 in a tissue layer and through the tissue puncture 118 into the vessel 128. The vessel includes an inner surface 129.

Referring now to FIGS. 5-14, an example tissue puncture closure device 200 is shown and described. The tissue puncture closure device 200 includes a carrier tube 202, a filament 204, a housing 206, an anchor assembly 208, a sealing member 210, a compaction member 212, and an auto compaction assembly 214. The carrier tube 202 may be advanced through a procedure sheath 216 and be connected to the insertion sheath with a plurality of connectors 215. The auto compaction assembly 214 may operate to automatically advance the compaction member 212 relative to the carrier tube 202 and procedure sheath 216 upon withdrawal of the housing 206 to compact the sealing member 210 toward the anchor assembly 208. The sealing member 210 may seal closed a tissue puncture 118 (see FIGS. 6-10) and sandwich a portion of a wall of a vessel 128 between the anchor assembly 208 and sealing member 210. While an automatically operating compaction assembly 214 is shown and described herein, other types of compaction assemblies, devices and methods may be used with the anchor assembly 208.

The anchor assembly 208 may include a first anchor portion 240 and a second anchor portion 242. The first anchor portion 240 may include a base 244, a plurality of petal members 246A-D, hinge members 248 operable between the base 244 and petal members 246A-D, and proximal and distal surfaces 250, 252 (see FIGS. 11-13). The base 244 may include an aperture 254 and a first tapered surface 256 leading to and defining, at least in part, the aperture 254. The first tapered surface 256 may be formed in the distal surface 252 and arranged to interface with a portion of the second anchor portion 242. In one example, the first tapered surface 256 includes a tapered angle that matches a tapered angle of an second tapered surface 270 of the second anchor portion 242 (see FIG. 7).

Figure 6:
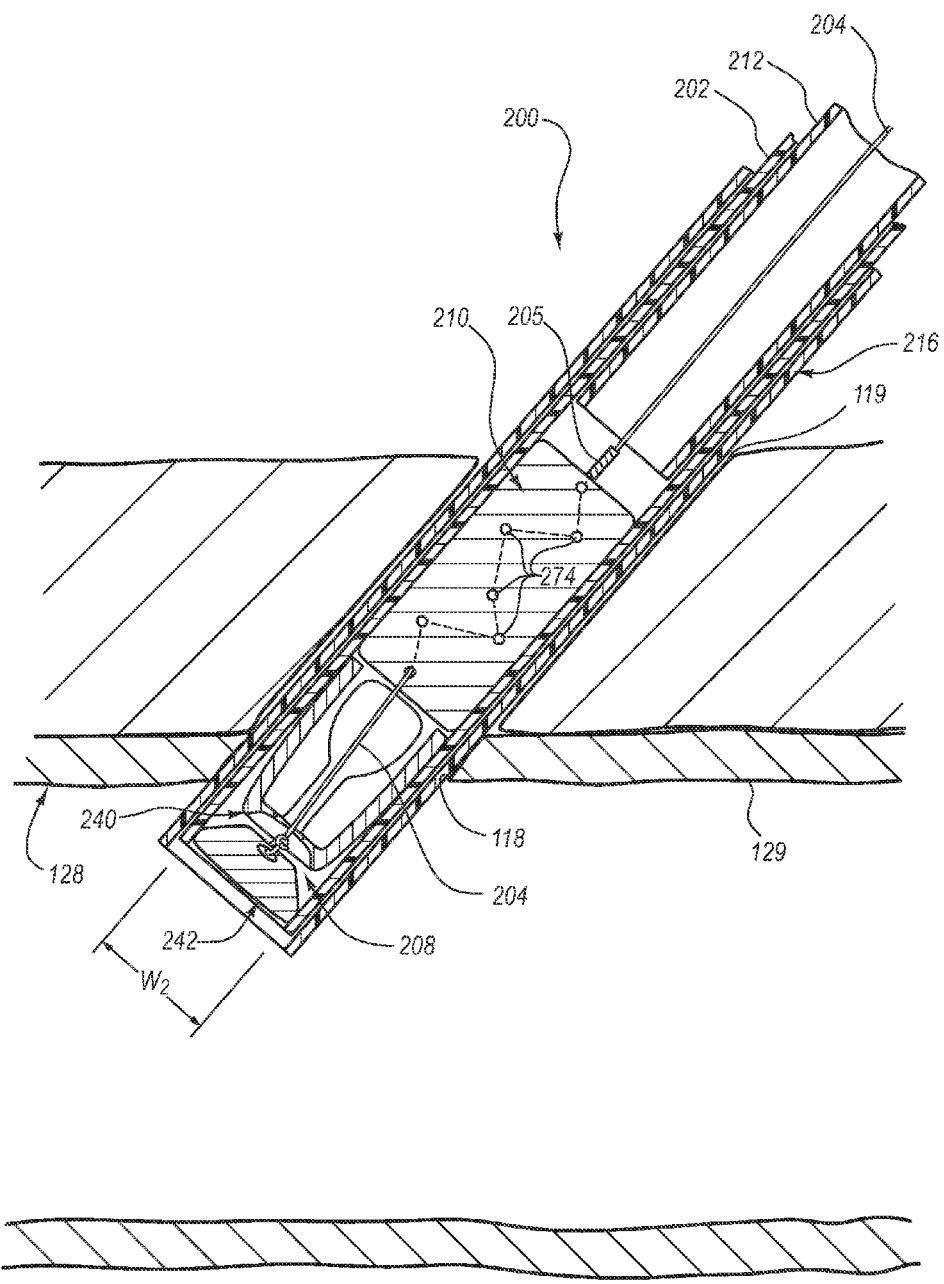
FIG. 6 is a cross-sectional side view of a distal end of the tissue puncture closure device of FIG. 5 inserted through a tissue puncture.

The petal members 246A-D may be connected to the base 244 at spaced apart locations around a periphery of the base 244. In some arrangements, the petal members 246A-D are equally spaced apart from each other, while in other arrangements, the petal members 246A-D are unequally spaced apart. The petal members 246A-D may have substantially the same size and shape. The petal members 246A-D may be connected to the base 244 using hinges 248. The hinge 248 may include a groove 264 and a protrusion 266. As shown in FIGS. 13 and 14, each of the hinges 248 comprise the groove 264 on a first planar surface of the hinge 248 and the protrusion 266 on a second planar surface opposite the first planar surface. A construction of the hinge 248 may permit the petal members 246A-D to pivot or bend in a single direction relative to the base 244 (e.g., in a proximal direction as shown in FIG. 6). Once the petal members 246A-D rotate from a retracted or pivoted position as shown in FIG. 6 to an expanded or extended position as shown in FIGS. 7-10, the petal members 246A-D do not pivot further in the distal direction. The petal members 246A-D may act as anchors within the vessel 128 to limit movement of the anchor assembly 208 back through the tissue puncture 118.

The petal members 246A-D may each include a neck portion 258, a petal portion 260, and a rib 262. The neck 258 may have a smaller width than a maximum width of the petal portions 260 (see FIGS. 11-12). The neck 258 may connect to the hinges 248. The petal portions 260 may have an increased surface area to provide improved contact and interface with an inner surface of the vessel adjacent to the tissue puncture 118. The petal portions 260 may be configured to at least partially bend or fold along a longitudinal axis X (see FIG. 11) of each petal portion to assist in positioning the petal members 246A-D within the carrier tube 202 (see FIG. 6). The rib 262 may provide additional rigidity for each of the petal portions 260 once the first anchor portion 240 is removed from the carrier tube 202 so that the petal members 246A-D remain in an expanded position as shown in FIGS. 7-14 without collapsing distally. The rib 262 may extend around an entire periphery of each of the petal portions 260. The rib 262 may extend along portions of the neck 258 and may terminate at the hinge 248. In some arrangements, the rib 262 may extend around only portions of the periphery of the first anchor portion 240, or at other location spaced inward from the periphery.

In other embodiments, the petal portion 260 and a neck 258 may have a constant width instead of having an increased width along the petal portions 260. The rib 262 may extend along different or additional portions of the neck 258 and pedal portion 260 such as, for example, at least one rib that extends parallel with and adjacent to the axis X.

The groove 264 and protrusion 266 of the hinge 248 may assist in providing pivotal movement of the petal members 246A-D into a retracted position relative to the base 244 in a single direction. The groove 264 may provide a reduced resistance to bending in the neck 258 that permits the petal members 246A-D to bend or pivot in a proximal direction for purposes of delivery of the first anchor portion 240 through the tissue puncture 118. The protrusion 266 may provide an increased resistance to pivoting or bending in the distal direction so that the first anchor portion 240 may provide an anchor function when expanded within the vessel 128.

The first anchor portion 240 has a maximum width $W_1$ when in the expanded position as shown in FIG. 12. Typically, the maximum width $W_1$ is greater than a maximum width of the tissue puncture 118. The first anchor portion 240 has a minimum width $W_2$ when in a refracted or compacted position when positioned within the carrier tube 202 (see FIG. 6). The retracted position for the first anchor portion 240 may also be referred to as a low profile position or low profile orientation used for delivery of the anchor assembly 208.

The first anchor portion 240 may be formed using a molding technique and may have a generally solid construction. Alternatively, the first anchor portion 240 may comprise a skeleton construction having a minimum amount of material. In a skeleton construction embodiment (e.g., the first anchor portion 440 shown in FIGS. 16-17), the petal members may be defined by a perimeter piece of material with a hollow interior portion. The first anchor portion may comprise a shape memory material such as, for example, Nitinol or a shape memory polymer.

The first anchor portion may have any desired number of petal portions. FIG. 15 shows one alternative embodiment of a first anchor portion 340 that includes first and second petal members 346A-B attached to a base 344. The first and second petal members 346A-B may be arranged directly opposite from each other and equally spaced around a periphery of the base 344. Other arrangements are possible including unequal spacing of the petal members 346A-B around a periphery of the base 344.

The petal members 346A-B may include suture holes 363. The suture holes 363 may be formed in the petal members 346A-B or on the base 344. The suture holes 363 may be used as alternative suture paths for sutures passing through the first anchor portion 340 rather than passing through aperture 354 of base 344.

FIGS. 16-17 illustrate another example first anchor portion 440 that includes a base 444 and three petal members 446A-C. The petal members 446A-C may be equally spaced apart around a periphery of the base 444. The first anchor portion 440 illustrates an example skeletal construction for the petal members 446A-C. The petal members 446 A-C may have a skeletal, frame-like structure and a hollow center. The base 444 includes an aperture 454 and a tapered surface 456 configured to receive a second anchor portion 242.

Referring now to FIGS. 6-10 and 18-20, the second anchor portion 242 includes a second tapered surface 270 and a suture aperture 272, and has a maximum width $W_3$. The second tapered surface 270 may be formed to mate with the first tapered surface 256 of the first anchor portion 240. A second tapered surface 270 may be arranged facing proximally to face and contact the distal surface 252 of the first anchor portion 240. The second tapered surface 270 may include a generally conical or truncated conical shape of the second anchor portion 242.

The suture aperture 272 may extend laterally through the second anchor portion 242. The suture aperture 272 may be sized to pass at least one suture through the second anchor portion 242 to provide a physical connection of a suture to the second anchor portion 242.

The maximum width $W_3$ (see FIG. 20) is typically greater than a maximum width $W_4$ of the first tapered surface 256 (see FIG. 13) and the aperture 254 of the first anchor portion 240. The second anchor portion 242, when drawn against the first anchor portion 240 and mating with the first tapered surface 256, plugs the aperture 254 to prevent fluid flow there between. The second tapered portion may be used to draw the first anchor portion 240 proximally into contact with an inner surface of the vessel 128 adjacent to the tissue puncture 118.

Typically, the second anchor portion 242 has a relatively small height $H_1$ (see FIG. 20) to minimize flow disruption within the vessel 128. The second anchor portion 242 may comprise a different material than the first anchor portion 240. In one example, the second anchor portion 242 comprises a rigid polymer such as polylactic-co-glycolic acid (PLGA). Both of the first and second anchor portions 240, 242 may comprise a bioresorbable material such as a bioresorbable polymer.

The first and second anchor portions 240, 242 may include an anti-coagulant coating such as, for example, heparin. Such a coating may limit thrombosis in view of the large amount of material of the anchor assembly 208, especially provided with the plurality of petal members 246A-D that are positioned within the vessel and exposed to blood flow. In some arrangements, anti-coagulant compounds may be embedded in the polymer material prior to forming the first and second anchor portions 240, 242. Other coatings are possible, including those that may increase endothelization while also limiting thrombosis.

Figure 7:
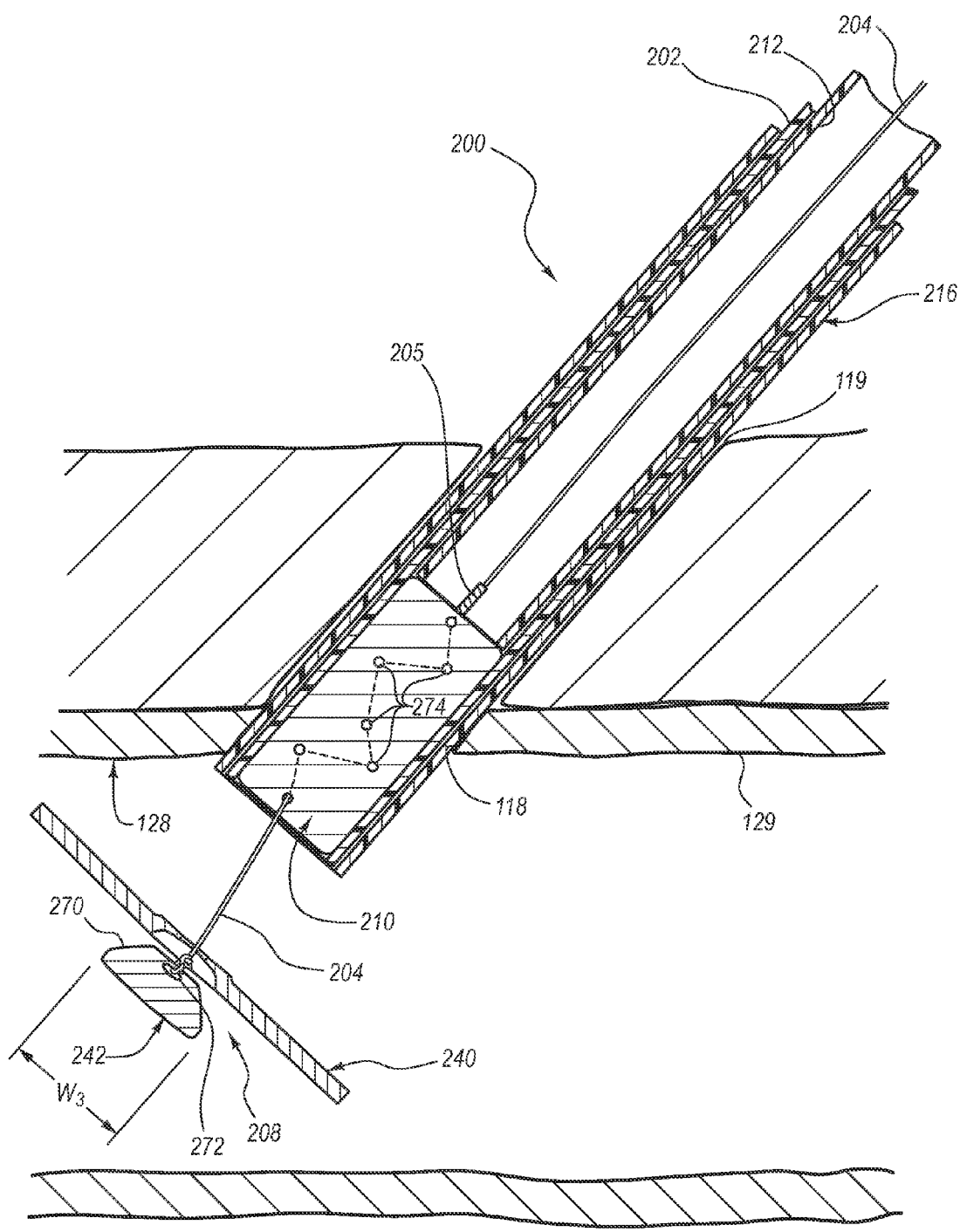
FIG. 7 is a cross-sectional side view of the distal end of the tissue puncture closure device of FIG. 6 with an anchor assembly deployed.
Figure 8:
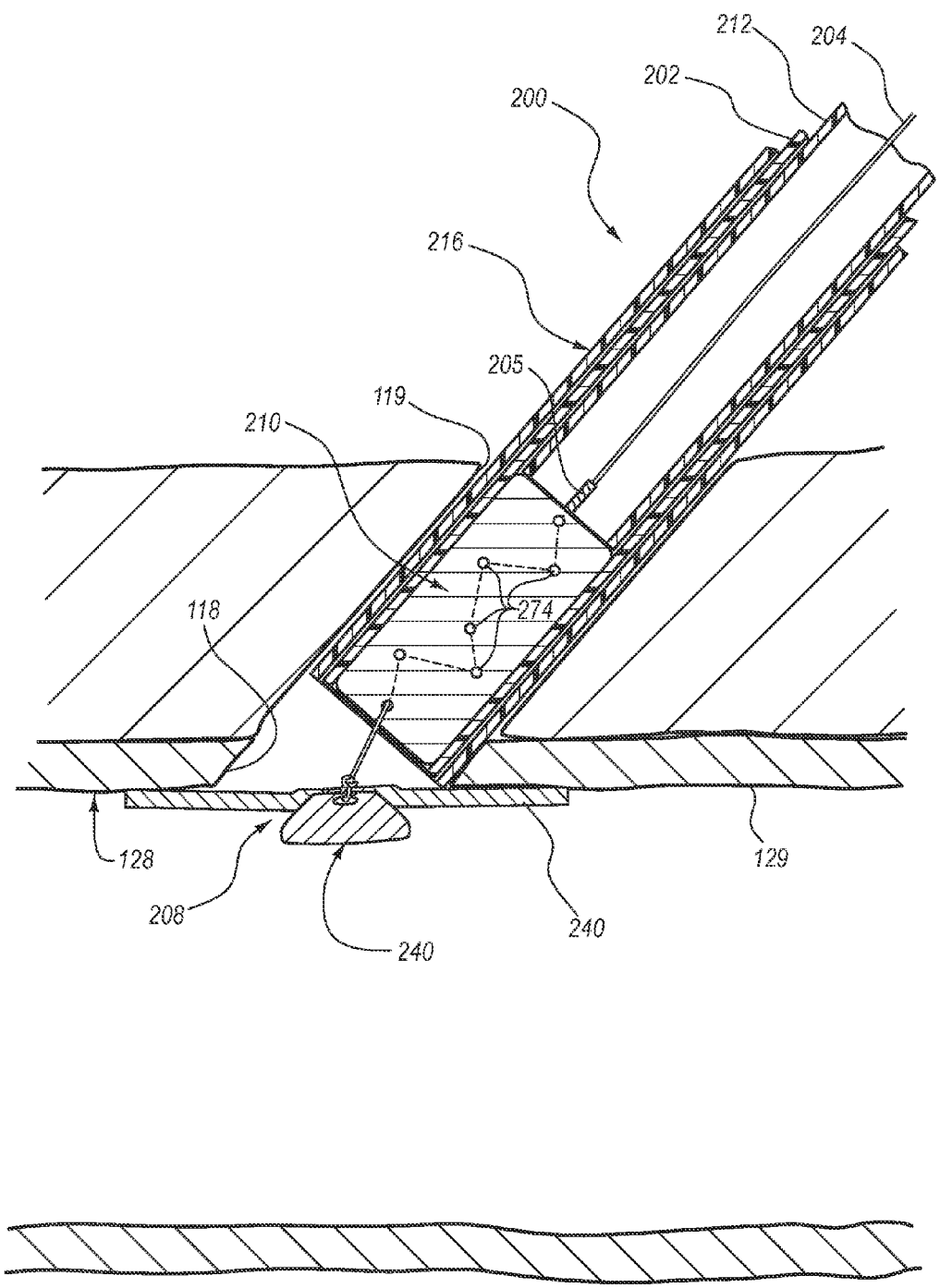
FIG. 8 is a cross-sectional side view of the tissue puncture closure device of FIG. 7 with the anchor assembly drawn into contact with an inner surface of the tissue.

Referring now to FIGS. 6-10, an example method of sealing closed a vessel puncture is described with reference to tissue puncture closure device 200. Referring first to FIG. 6, the procedure sheath 216 is advanced through a percutaneous incision 119 and tissue puncture 118 into a vessel 128. The carrier tube 202, which has positioned therein the anchor assembly 208, sealing member 210 and compaction member 212, is advanced through the procedure sheath 216 and into the tissue puncture 118. The anchor assembly 208 is disposed out of the carrier tube 202 and into the vessel 128 as shown in FIG. 7. The first anchor portion 240 may automatically move from the retracted, low profile position within the carrier tube 202 shown in FIG. 6 to an expanded position once expelled from the carrier tube 202 as shown in FIG. 7.

The filament 204 is connected to the second anchor portion 242. The filament 204 extends through the aperture 254 in the first anchor portion 240, through a weave pattern in the sealing member 210 defined by a plurality of holes 274, and extends proximal of the sealing member 210 to the auto compaction assembly 214. A knot 205 may be formed in the filament 204 and positioned proximal of and adjacent to the sealing member 210. The knot 205 may be a slip knot which, when advanced along the filament 204, maintains pressure on the sealing member 210 and maintains a position of the sealing member 210 relative to the filament 204 and anchor assembly 208.

The entire tissue puncture closure device 200 may then be withdrawn until the first anchor portion 240 is pulled by the filament 204 against an inner surface 129 of the vessel 128 by the second anchor portion 242. The one-way hinges 248 of the first anchor portion 240 are configured to limit movement of the petal members 246A-D distally in order to maintain the anchoring function against the inner surface 129.

Figure 9:
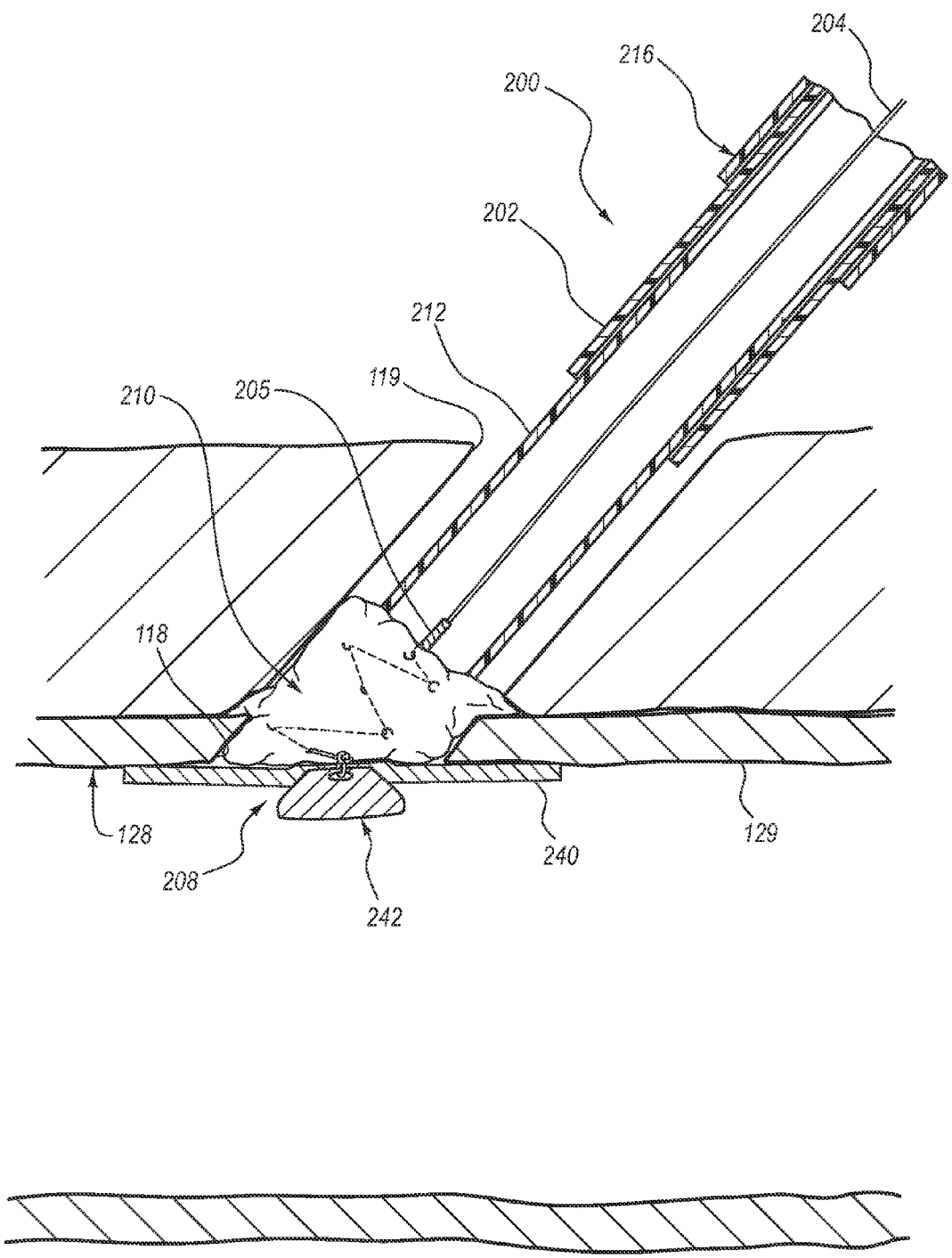
FIG. 9 is a cross-sectional side view of the tissue puncture closure device of FIG. 8 with a sealing member compacted against the anchor assembly.

The tissue puncture closure device 200 is withdrawn further in the proximal direction to activate the auto compaction assembly 214 to advance the compaction member 212 to compact or compress the sealing member 210 against the anchor assembly 208. The auto compaction assembly 214 may concurrently retract the procedure sheath 216 and carrier tube 202 while advancing the compaction member 212. The sealing member 210, when compacted as shown in FIG. 9, may fill the tissue puncture 118 and at least a portion of the percutaneous incision 119. The sealing member 210 may absorb fluids such as any blood that is within the percutaneous incision 119 and expand to seal closed the tissue puncture 118. The knot 205 may be advanced along the filament 204 while advancing the compaction member 212. The knot 205 may help hold the sealing member 210 in the compacted position shown in FIG. 9.

Figure 10:
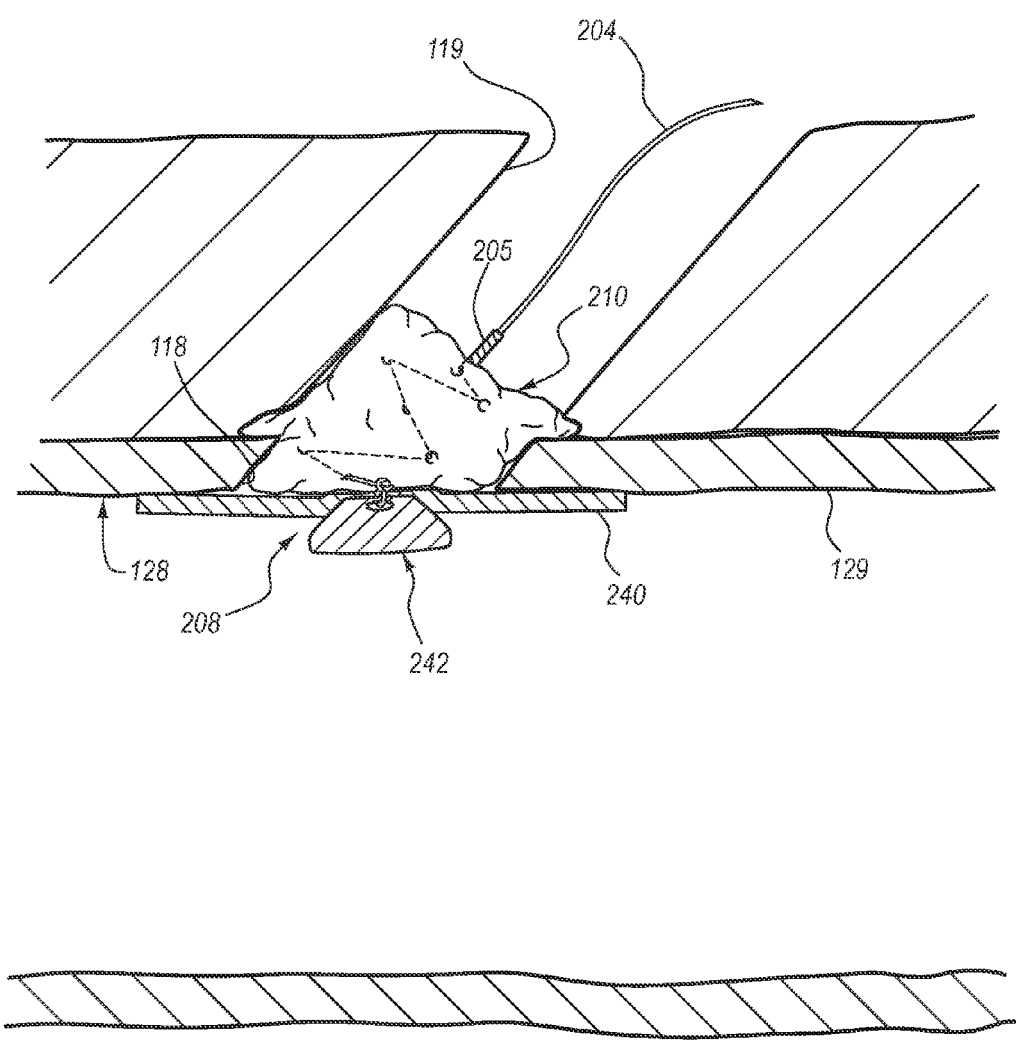
FIG. 10 shows the tissue puncture of FIGS. 6-9 sealed closed.

The auto compaction assembly 214 may then be disengaged so that the carrier tube 202, compaction member 212, and procedure sheath 216 may be removed from the patient. The filament 204 is cut as shown in FIG. 10.

Some example auto compaction assemblies that are suitable for use with the closure device 200 are described in U.S. Pat. Nos. 7,931,670; 7,618,438; and 7,250,057, which patents are incorporated herein in their entireties by this reference.

The tissue puncture closure device 200 is configured to seal closed a vessel puncture using a two-piece anchor assembly that is positioned within a vessel and a compaction assembly that sandwiches a wall of the vessel between a sealing member that is positioned outside of the vessel and the anchor assembly. A first portion of the anchor assembly (also referred to as plug) has a suture attached thereto with the suture extending through an aperture in the other anchor portion. Applying tension to the suture draws the plug against a seat in the other anchor portion and against an internal wall of the vessel. An interface between the two anchor portions may provide a fluid-tight configuration for the anchor assembly and may temporarily seal closed a vessel puncture when the anchor assembly is drawn against an internal surface of the vessel and overlapping the vessel puncture. The first anchor portion may isolate the second anchor portion from contracting the vessel.

The anchor assembly may operate between a refracted, low profile position when delivered through the vessel puncture, and an expanded large profile position to provide an anchor function within the vessel. The anchor assembly may be particularly useful for large bore closures of at least 10 French in size.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure system, comprising:
   a suture;
   an anchor assembly comprising:
      a first anchor portion having a base member and a plurality of petal members extending peripherally spaced around the base member, the base member comprising a first tapered surface, the plurality of petal members being automatically expandable from a retracted position for delivery through a vessel puncture in a vessel, and an expanded position when deployed within the vessel, the first anchor portion having a first width when in the retracted position, each of the plurality of petal members having a periphery and a stiffening rib extending around the periphery, each of the plurality of petal members being connected to the base member by a hinge, each of the stiffening ribs terminating at the hinges, each of the hinges comprising a groove on a first planar surface of the hinge and a protrusion on a second planar surface of the hinge opposite the first planar surface;
      a second anchor portion connected to the suture and positioned distal of the first anchor portion within the vessel, the second anchor portion comprising a second tapered surface, the second anchor portion having a second width, the second width being about equal to the first width;
   wherein withdrawing the suture pulls the second tapered surface of the second anchor portion against the first tapered surface of the first anchor portion to receive the first and second tapered surfaces against each other and to bring into contact the first anchor portion against an inner surface of the vessel adjacent to the vessel puncture.

2. A vascular closure system according to claim 1, wherein the plurality of petal members are oriented perpendicular to a longitudinal dimension of the anchor assembly when in the expanded position.

3. A vascular closure system according to claim 1, wherein the plurality of petal members extend proximally when in the retracted position.

4. A vascular closure system according to claim 1, wherein the plurality of petal members pivot in a single direction from the expanded position to the retracted position.

5. A vascular closure system according to claim 1, wherein each of the hinges comprises a living hinge.

6. A vascular closure system according to claim 1, wherein the first anchor portion includes an aperture defined within the first tapered surface.

7. A vascular closure system according to claim 1, wherein the first and second anchor portions are separate and distinct pieces.

8. A vascular closure system according to claim 1, wherein the second anchor portion includes a suture through hole configured for connecting the suture to the second anchor portion.

9. A vascular closure system according to claim 1, wherein at least some of the plurality of petal members include a suture aperture configured to pass a suture there through.

10. A vascular closure device, comprising:
    a suture;
    a two-piece anchor assembly, comprising:
       a first anchor portion having a base member and a plurality of petal members extending peripherally spaced around the base member, the base member comprising a first tapered surface, the plurality of petal members being configured to pivot into an expanded position upon positioning in a vessel, each of the plurality of petal members having a periphery and a stiffening rib extending around the periphery, each of the plurality of petal members being connected to the base member by a hinge, each of the stiffening ribs terminating at the hinges, each of the hinges comprising a groove on a first planar surface of the hinge and a protrusion on a second planar surface of the hinge opposite the first planar surface;
       a second anchor portion connected to the suture and configured to draw the first anchor portion against an inner surface of the vessel upon withdrawal of the second anchor portion, the second anchor portion comprising a second tapered surface, the second tapered surface being configured to contact the first tapered surface of the base member;
    a sealing member configured to advance along the suture and compact against the anchor assembly to seal closed a vessel puncture.

11. A vascular closure device according to claim 10, wherein the plurality of petal members each include a neck portion and a petal portion, the neck portion having a smaller maximum width than a maximum width of the petal portion.

12. A vascular closure device according to claim 10, wherein the first anchor portion comprises a shape memory material.

13. A vascular closure device according to claim 10, wherein the first anchor portion has a larger profile when in the expanded position than a profile of the second anchor portion.

* * * * *